United States Patent [19]

De Pedro

[11] 4,177,818
[45] Dec. 11, 1979

[54] SELF ATTACHABLE SMALL-TOOTHED ELECTRODE AND A FORCEPS FOR MANEUVERING IT

[76] Inventor: Francisco L. De Pedro, Segurola 1431, 2nd Floor, Apt. "H", 1638 Vicente López, Argentina

[21] Appl. No.: 857,845

[22] Filed: Dec. 5, 1977

[30] Foreign Application Priority Data

Dec. 2, 1976 [AR] Argentina ............................... 265699

[51] Int. Cl.$^2$ ................................................ A61N 1/04
[52] U.S. Cl. .................................. 128/418; 128/419 P
[58] Field of Search ....................... 128/418, 419 P, 404, 128/337, 346

[56] References Cited

U.S. PATENT DOCUMENTS

| | | | |
|---|---|---|---|
| 3,216,424 | 11/1965 | Chardack | 128/418 |
| 3,604,425 | 9/1971 | Le Roy | 128/346 X |
| 3,978,865 | 9/1976 | Trabucco | 128/419 P |
| 4,058,128 | 11/1977 | Frank et al. | 128/418 |
| 4,066,085 | 1/1978 | Hess | 128/418 |

FOREIGN PATENT DOCUMENTS 1575665 6/1969 France .................................. 128/419 P

*Primary Examiner*—Lee S. Cohen
*Attorney, Agent, or Firm*—Ladas, Parry, Von Gehr, Goldsmith & Deschamps

[57] ABSTRACT

An electrode carrying member which is inserted with forceps into the epicardial muscle and which comprises a substantially parallepipedic elastic body having two large planar faces; two parallel long sides and two parallel short sides, a conductor attached to the first one of the large faces; four small inwardly curved teeth attached to the second large face close to the corners thereof; each tooth having a sharpened thin point; the teeth next to each of the long sides being arranged in a straight line running parallel to said long sides with the points of opposing pairs of teeth directed towards each other and forming an arc of a circle separated by a gap; a thin electrode point projecting from the center of the second large face midway between said opposing pairs of teeth; a stub projecting from each of the short parallel sides and receptacles on the forceps receiving the stubs. Prior to insertion the stubs are placed in the receptacles of the forceps and on manually closing the forceps, the elastic body is bent back on itself until the curved teeth are substantially parallel one with the other and parallel to the electrode point so as to permit their being driven into the heart muscle without tearing the muscle and on releasing the forceps the elastic body being allowed to resume its original shape causing the curved teeth to be further embedded in the heart muscle with minimum damage to the tissue.

1 Claim, 8 Drawing Figures

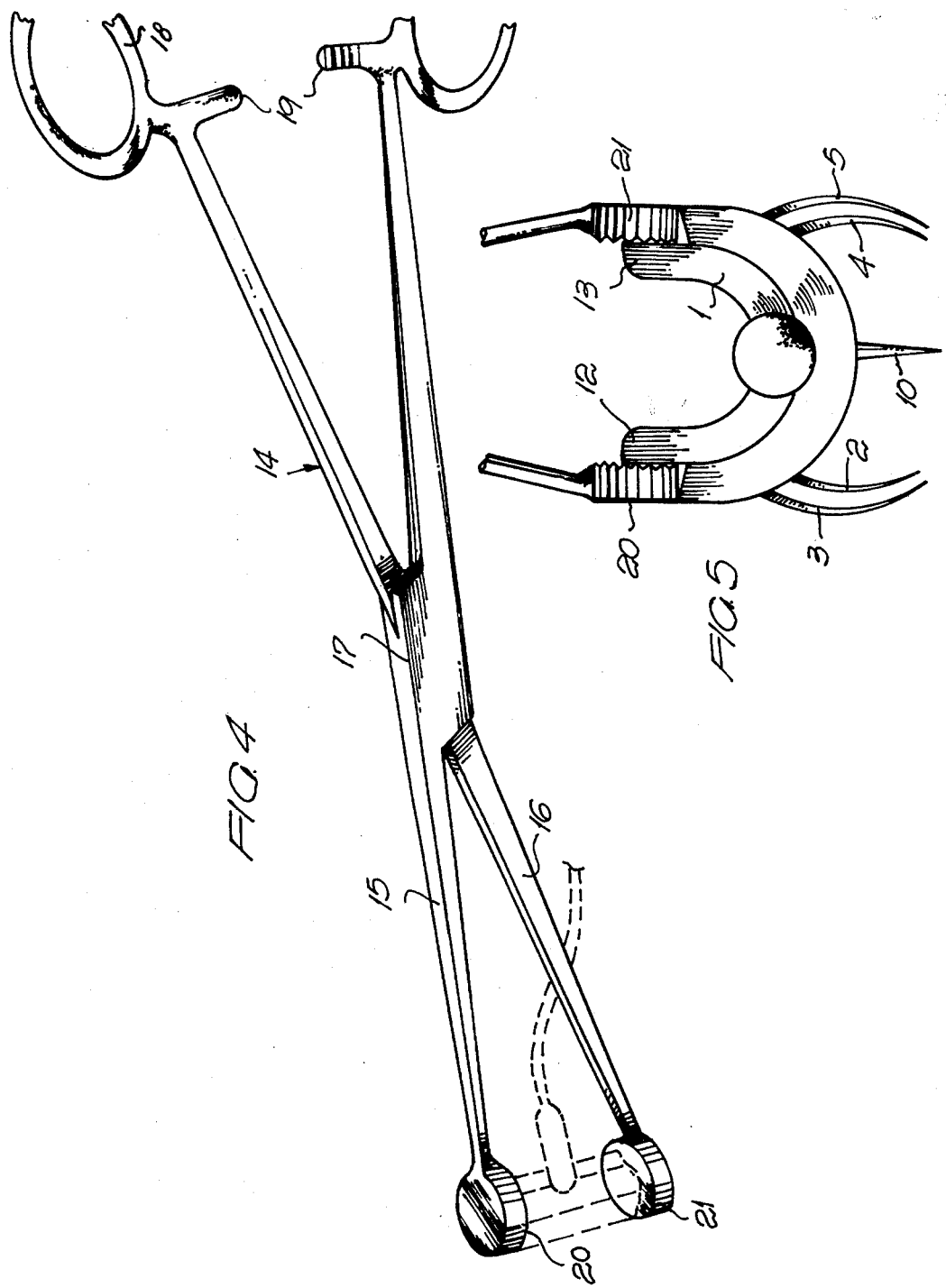

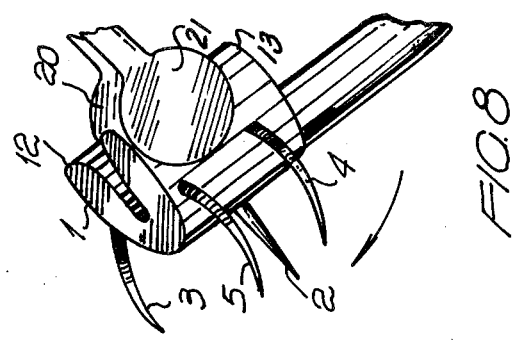
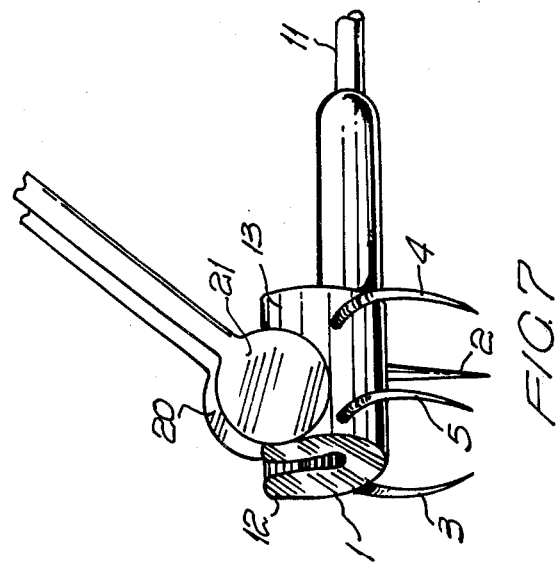
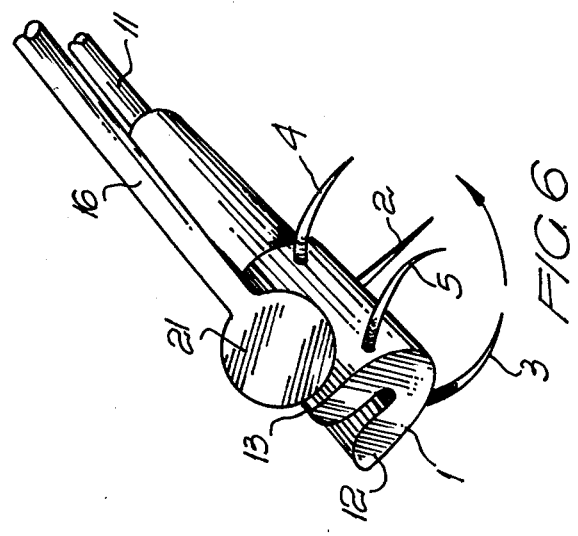

SELF ATTACHABLE SMALL-TOOTHED ELECTRODE AND A FORCEPS FOR MANEUVERING IT

The present invention is related to "a self-attachable small-toothed electrode and a forceps for maneuvering it", the main object thereof being to provide an electrode particularly adequate for its implantation in the heart muscle, by means of which, together with its corresponding maneuvering forceps the drawbacks shown by the previously known electrodes when carrying out the same purpose are eliminated.

This electrode is designed and thought to compensate the disadvantages found when implanting the already known electrodes in the epicardial muscle, where the field is almost always very small and the maneuvering is dangerous due to poor vision. It was sought, as an objective, to embody an electrode with the characteristic of attaching itself to the heart muscle by a high-precision, rapid and easely executable maneuver, avoiding or minimizing the error of positioning and the risks of tearing out the right ventricle, which is the approachable one when using this route. The second objective was the attainment of a sure implantation of the electrode, so that it would not move after its positioning, affording in such a manner safety during the operation and the avoidance of new operations to relocate it. The third object was, although it seem contradictory with respect to the foregoing, to attain that in the very particular cases wherein there was no other solution than withdrawing the electrode (infection, bad threshold, wrong election of the implantation site, etc.) this could be effected with minimum possible traumatism, and with a safe and precisa maneuvering which is fully obtained with the adaptation of the electrode and the forceps. The fourth objective is to obtain a threshold of the least possible magnitude, since a longer life of the pacemaker and a surer and better stimulation and synchronization, in the case of a Synchronized Pacemaker, is reached in this manner.

For a better understanding and a simplified practice of the invention, it has been represented in its preferred embodiment by the accompanying drawings, wherein:

FIG. 4 is a perspective view of the forceps, which is combined with the electrode of the invention for the maneuvering thereof, and FIGS. 5 to 8 show the different positions corresponding to the gripping of the forceps and the electrode to adapt them to the needs of the surgical field.

In all the figures, similar or corresponding parts of the invention are shown by the same reference numbers; the invention comprises a body 1 of the electrode, made of a resilient material, preferably "Silastic", of a substantially parallelepipedic configuration; in one of its larger faces there are secured, in a position adjacent to the vertices thereof, four small teeth, preferably of a circular section, as shown by 2, 3, 4 and 5.

Figure 1:
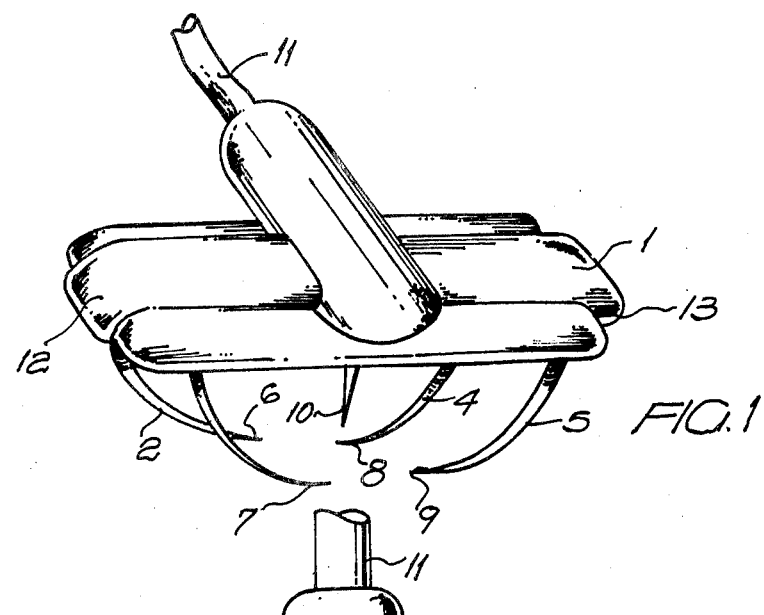
FIG. 1 is a perspective view of the small-toothed electrode of the invention in its unipolar version.
Figure 2:
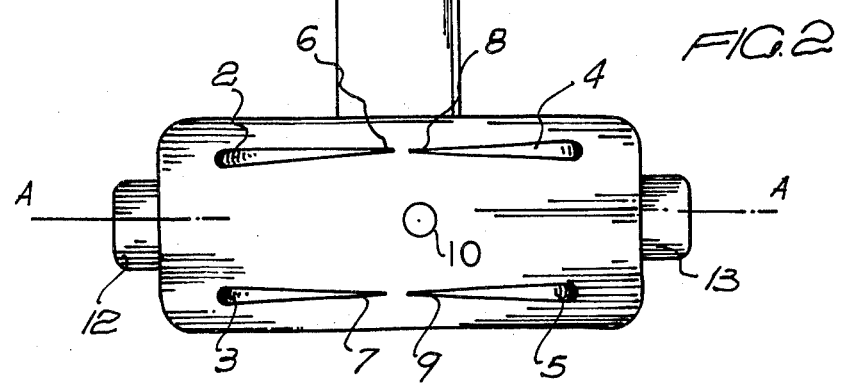
FIG. 2 is a plan view of the face of the electrode of the invention, provided with said small teeth.
Figure 3:
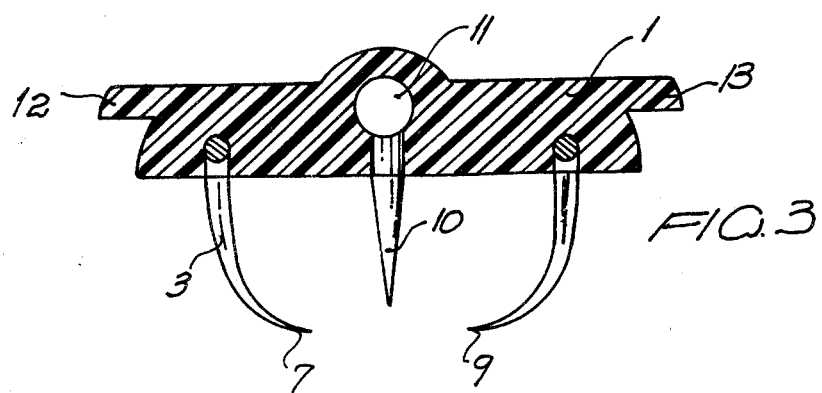
FIG. 3 is a sectional view by line-A—A of FIG. 2.

Each pair of said small teeth are in a plane substantially perpendicular to said face and each tooth has its axis contained in said plane, said axis being smoothly curved in such a manner that the ends 6, 7 and 8, 9 of the small teeth in each pair are one in front of the other, determining a straight line substantially parallel to said face. Furthermore, said ends are sharpened, forming thin points and it can be appreciated, in FIG. 3, that each pair of small teeth 2, 3 and 4, 5 has its axis incurved, forming portions of an arc of circle with their ends separated.

A thin point 10 (omitted for the sake of clarity from FIGS. 6–8) is projected from the center of the face having said small teeth implanted, with the axis substantially perpendicular to the plane of said face, the point corresponding to the unipolar version of the electrode, but in the bipolar version, it can be repeated, point 10 constituting the myocardium stimulator, by the effect of the current delivered by the pacemaker, to which it is connected, by means of conductor 11 and collecting the potential produced by the ventricle for synchronization.

Laterally, from the faces of lesser length, corresponding stubs 12, 13 are projected, the purpose of which is to easily and completely adapt themselves to the positioning forceps 14, even while the heart is in movement, which is considered an extremely favourable characteristic of the invention.

The forceps 14 is constituted by two branches 15, 16 articulated at 17, which in one of their ends have the manual handling loops 18 and adjacent to them locks 19, wherein a determined angular position of the branches 15 and 16 is marked, the branches being provided at their other ends with the receptacles 20, 21 wherein the stubs 12 and 13 are inserted during the maneuvering of the electrode.

By placing the stubs 12 and 13 in the receptacles 20 and 21, the effort necessary to close the forceps is effected manually on the loops 18, until the markings of the locks 19 coincide.

This action will bend body 1, until it is carried up to the position shown in FIG. 5, wherein the end of the pairs of small teeth are substantially in a position which is parallel one with the other and parallel to the point, or points, 10, which permits their being driven into the heart muscle or their easy withdrawal in the case that the electrode is implanted therein, since due to the position of the extremes of the small teeth and the point, or points, no tearings out of the heart muscle can take place.

By FIGS. 5 to 8 it can easily be seen that during the positioning, the electrode is mounted and bent on the positioning forceps, which permits a perfectly modifiable articulation between the electrode head and the axis of said forceps, to adapt the electrode to every imaginable position which can happen in the surgical field. The electrode is placed in front of the previously elected zone of the myocardium (without any vessels or grease) and the small teeth and the electrode point are firmly rested on the myocardial muscle, smoothly unlocking the forceps then; this determined that, by its own elasticity, body 1 returns to its normal position, with the small teeth remaining implanted in the wall of the myocardial muscle; it should be seen that the lines of force deriving from the curvature of the small teeth, make that when the electrode cable is pulled, the small teeth are more deeply implanted. The "measure" of the electrode limits a zone of the myocardium of a semicylindrical form (lingitudinally sectioned) wherein the electrode or electrodes are always driven into, which area should always ideally maintain its structure and circulation in the maximum possible extent. This arrangement, with its small teeth which when closing remind the well known course of the old system of cables "stitched" with atraumatic needle and thread, so well proven in the surgical and medical practice, adds the advantage of not producing, on the limits of the electrode plate, two solid inextensible loops of stitching material that do not yield and undoubtedly suffocates a great portion of the circulation destined to such a minute but essential area where it is sought to be stimulated as long as possible with the best threshold.

As the electrode of the invention has a flexible body, the chance of maintaining the delicate heart tissues intact are very high, avoiding in this manner the occurrence of infarctions or hypoirrigated zones in such a critical point.

I claim:

1. The combination of an electrode carrying member which is adapted to be inserted with hooks into the cardiac muscle and specially shaped forceps to assist in such insertion wherein the improvement comprises:
   (a) a substantially parallepipedic elastic body having first and second large planar faces and two parallel long sides and two parallel short sides;
   (b) a conductor attached to the first one of the said large faces;
   (c) four small inwardly curved teeth attached to the second large face close to the corners thereof;
   (d) each tooth having a sharpened thin point;
   (e) the teeth next to each of the long sides being arranged in a straight line running parallel to said long sides with the points of opposing pairs of teeth directed towards each other and said opposing pairs of teeth forming an arc of a circle separated by a gap;
   (f) a thin electrode point connected to the conductor projecting from the center of the second large face midway between said opposing pairs of teeth;
   (g) a stub projecting from each of the short parallel sides of the elastic body;
   (h) receptacles at the free ends of said forceps receiving said stubs to permit articulation between the elastic body and said forceps; the arrangement being such that prior to insertion of the electrode the said stubs are placed in said receptacles formed at the ends of the forceps and on manually closing the forceps, the elastic body is bent back on itself until the curved teeth are substantially parallel one with the other and parallel to the electrode point so as to permit their being driven into the heart muscle without tearing the muscle and on releasing the forceps, the elastic body is allowed to resume its original shape causing the curved teeth to be further embedded in the heart muscle with minimum damage to the tissue.

* * * * *